United States Patent [19]

Zollinger

[11] 4,103,722

[45] Aug. 1, 1978

[54] APPARATUS FOR SEQUENTIALLY TREATING ONE OR MORE SPECIMENS OF CELLULAR MATERIAL WITH A PLURALITY OF TREATING LIQUIDS

[76] Inventor: Max Zollinger, 7589 de Normanville, Montreal, Quebec, Canada

[21] Appl. No.: 716,780

[22] Filed: Aug. 23, 1976

[51] Int. Cl.² .............................................. B65B 3/14
[52] U.S. Cl. ...................................... 141/70; 141/82; 141/104; 141/107; 141/284; 195/127; 222/136; 222/144
[58] Field of Search ................. 141/9, 11, 70, 82, 100, 141/104, 105, 130, 131, 69, 74, 107, 237, 242, 284, 367, 392; 68/207; 23/259; 137/561 A; 222/136, 144, 394; 195/127

[56] References Cited

U.S. PATENT DOCUMENTS

3,599,451   8/1971   Getz et al. .............................. 68/207

Primary Examiner—Richard E. Aegerter
Assistant Examiner—Frederick R. Schmidt
Attorney, Agent, or Firm—Raymond A. Robic; Francis B. Francois; Arthur Schwartz

[57] ABSTRACT

An apparatus for sequentially treating one or more specimens of cellular material with a plurality of treating liquids. The specimens are mounted in one or more treating chambers and the liquids in storage cylinders. Means selectively connect the storage cylinders to the treating chambers to selectively treat the specimens with the liquids.

7 Claims, 7 Drawing Figures

APPARATUS FOR SEQUENTIALLY TREATING ONE OR MORE SPECIMENS OF CELLULAR MATERIAL WITH A PLURALITY OF TREATING LIQUIDS

This invention is concerned with a method and an apparatus for use in treating specimens of cellular material.

Specimens of cellular material, such as animal tissue, are treated in laboratories for various purposes. For example, the specimen tissue may require microscopic examination and, to this end, it must usually be first treated with specific liquids, usually in a specific sequence, and for a specific length of time, in order to obtain the best examination results. In another manner of treatment, it may be desired to grow a culture on specimen tissue, and to this end the tissue may have to be immersed in several solutions, for specific periods of time. In a further manner of treatment, it may be desired to fix and dehydrate cells or cellular material by treating the material with adequate solutions. The specimens may also be subjected to various liquids in a specific sequence to treat the specimens for signs of certain diseases.

Presently, cellular material is usually treated in laboratories on a manual basis. To prepare a tissue specimen for microscopic examination for example, a laboratory technician will manually immerse and wash the specimen in various solutions for specific periods of time. The specimen is manually placed in, and removed from, each solution and its length of stay in the solution is timed. The preparation of the specimen in this manner is time consuming and subject to error if one step in the procedure is forgotten or inadvertently changed by the technician, or if a mistake in timing is made.

It is therefore a purpose of the present invention to provide a method, and an apparatus, for use in treating specimens of cellular material in a manner which minimizes manual handling and which mainimzes the chance of error. The apparatus according to the present invention can automatically treat one or a plurality of specimens at one time. The apparatus further can automatically treat the specimens with a specific sequence of liquids, the length of time each specific liquid treatment lasts also being automatically controlled.

In accordance with the present invention, an apparatus is provided with means for mounting one, and preferably a plurality of, specimens of cellular material. The mounted specimens are placed in special treating chambers in the apparatus. The apparatus has means for storing two or more different treating liquids. Means are provided for conducting, in sequence, a quantity of each liquid from its storing means to the treating chambers to treat the mounted specimens with each liquid. The length of the treatment periods can vary and can be automatically timed. Means are also provided for removing each liquid from the treating chamber after it has treated the specimens.

With the apparatus of the present invention, the major portion of treatment process can be automatically controlled. This eliminates the need for the constant presence of a technician to carry out, and time, each step in the process. Human error is thus minimized. The entire treatment process is also speeded up since the apparatus is capable of handling a plurality of specimens at one time. The apparatus employed is compact, and relatively simple in construction and use.

More especially, the subject invention is directed to an apparatus for use in treating cellular material which has chamber means for receiving at least one mounted specimen of cellular material. The apparatus also has means for separately storing at least two liquids used in treating the specimens, means for selectively connecting the liquid storing means with the chamber means, and means for moving the selected liquid from the storage means to the chamber means so that the mounted specimen can be treated with a selected liquid from the storage means.

According to a preferred embodiment, the liquid storing means comprises a holding member, and a plurality of storage cylinders in the holding member for holding the plurality of liquids. A main liquid outlet is provided in the holding member and a liquid outlet is provided in each cylinder. A conduit connects each cylinder outlet to the main outlet.

According to another preferred embodiment, the chamber means comprises a plurality of chambers arranged in a circle, each chamber having a bottom closed by a support which is permeable to air and liquid and a top liquid inlet.

The invention is also directed to a method for treating specimens of cellular material using the apparatus according to the invention, which method comprises the steps of: placing the specimens to be treated in chamber means; placing at least two different liquids in storage means and moving the liquids, in selected sequence from their storage means to the chamber means to treat the specimens.

The invention will now be described in detail having reference to the accompanying drawings in which.

Figure 1:
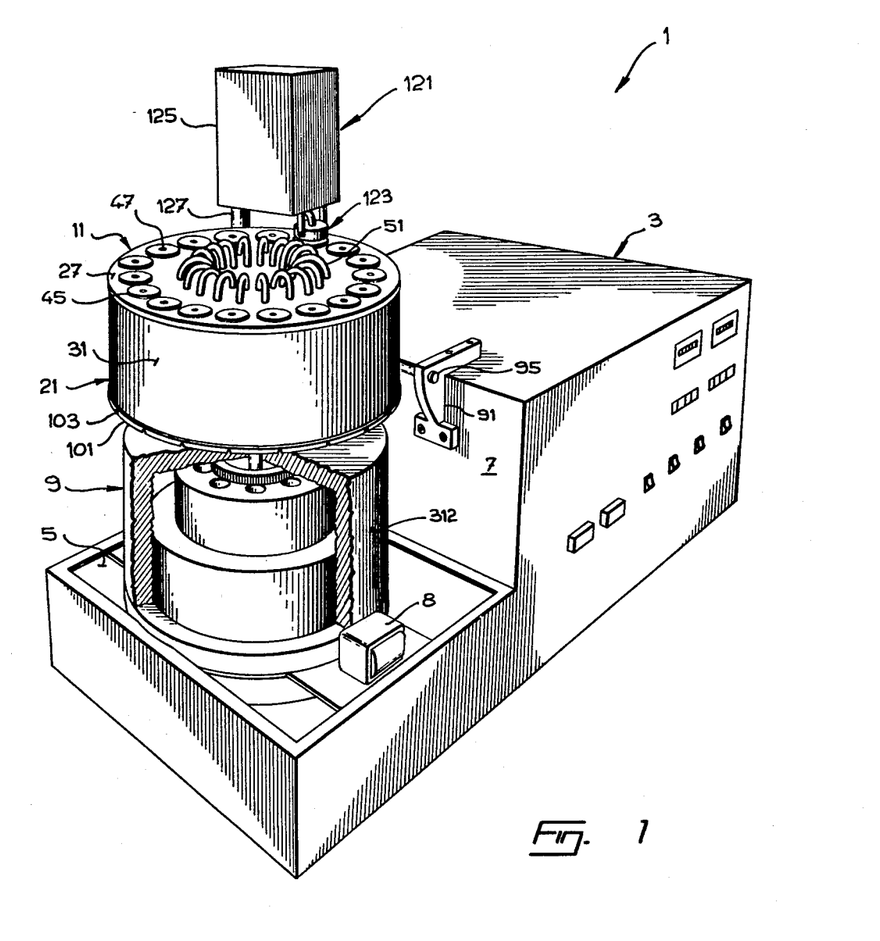
FIG. 1 is a perspective view of the apparatus.

The apparatus 1 of the present invention, for use in treating tissue specimens, comprises, as shown in FIG. 1, a cabinet 3 with a support shelf 5 extending from one side 7 thereof. The cabinet 3 and shelf 5 house various operating and control components as will be described.

The apparatus 1 also comprises a tissue treatment component 9 mounted on shelf 5, and a liquid supply component 11 mounted on top of the tissue treatment component 9.

Figure 2:
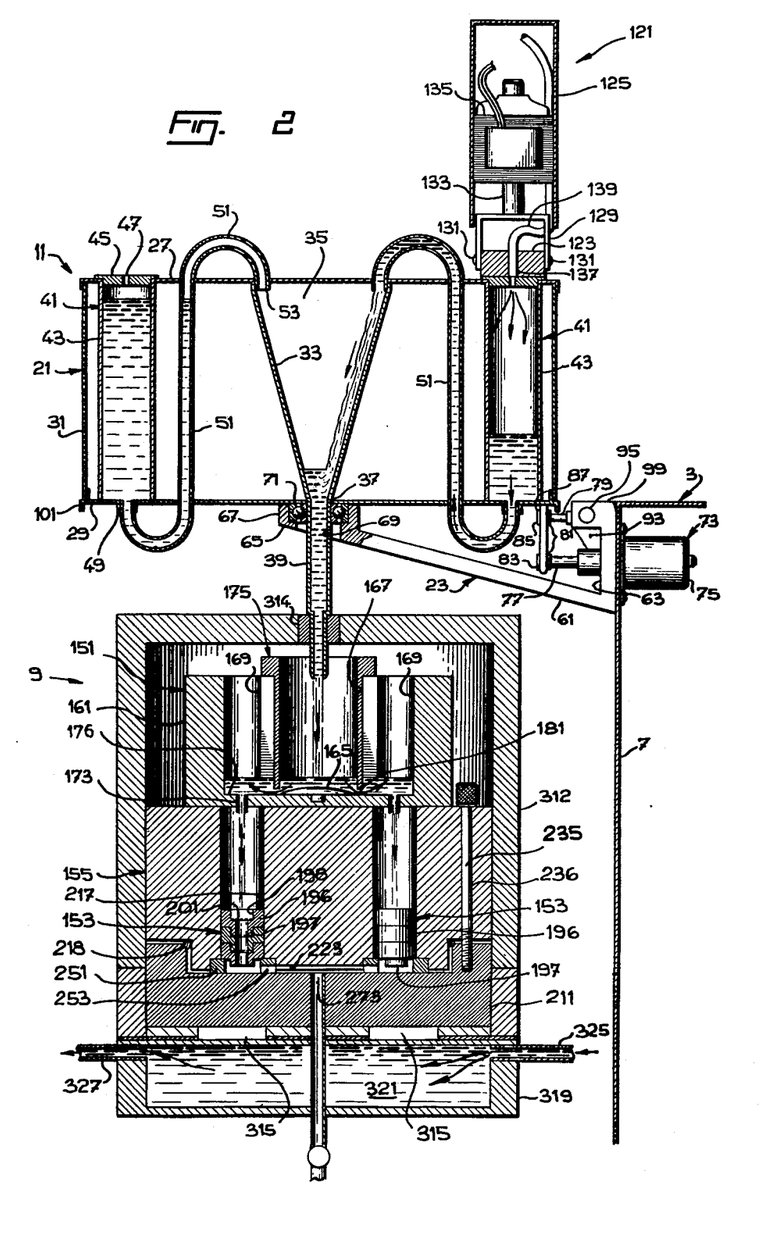
FIG. 2 is a cross-sectional view of the liquid supply and treatment components of the apparatus.
Figure 4:
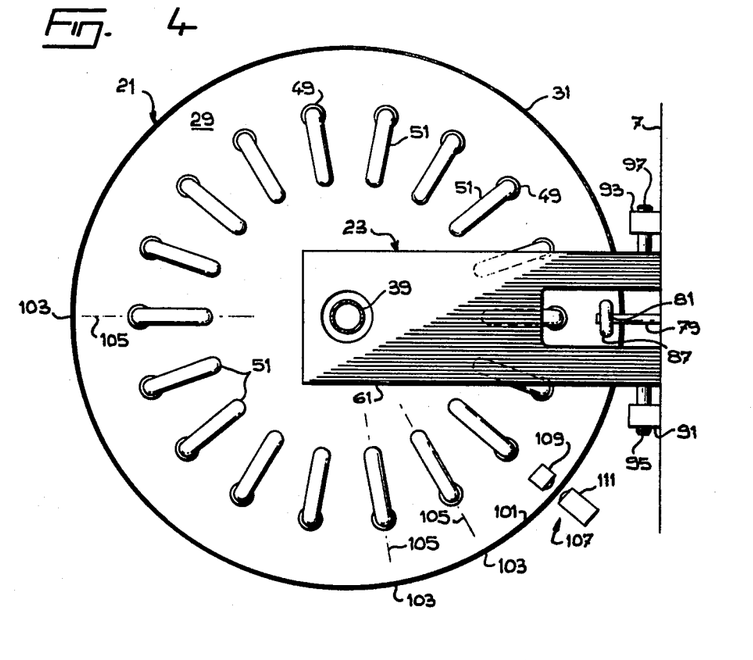
FIG. 4 is a bottom view of the liquid supply component.
Figure 5:
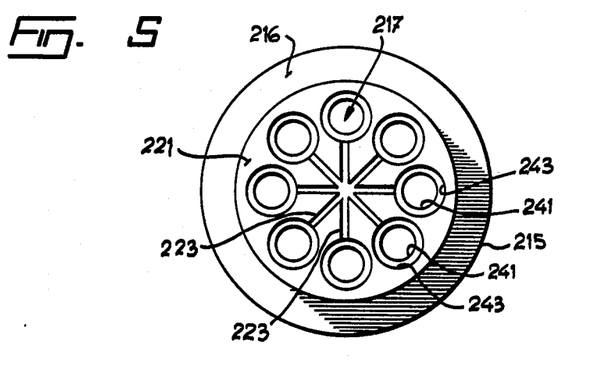
FIG. 5 is a bottom view of the treatment component.

The liquid supply component 11, as shown in FIGS. 1, 2 and 4, comprises a cylindrical liquid holder 21 mounted on a support arm 23. The support arm 23 is mounted on the one side 7 of the cabinet as will be described. The holder 21 has a top wall 27, a bottom wall 29, and a circular side wall 31. A funnel 33 is provided in the center of holder 21, extending from the top wall 27 down through the holder and out past the bottom wall 29. The large open inlet end 35 of funnel 33 is located at, and accessible through, the top wall 27. The funnel 33 tapers down to a small, outlet end 37 at bottom wall 29. A narrow tubular extension 39 projects down from outlet end 37 through bottom wall 29, and support arm 23, into the tissue treatment component 9.

A plurality of liquid chambers 41 are mounted in a circle in holder 21 adjacent side wall 31. The chambers 41 preferably comprise cylindrical tubes 43 extending between the top and bottom walls 27, 29. The open top of each cylinder 43 is closed by a tight fitting, removable cover 45. The cover 45 has a central through hole 47 leading into cylinder 43. Each cylinder 43 also has a bottom outlet 49 extending through bottom wall 29 of holder 21. A tube 51 is connected to each bottom outlet 49. Each tube 51 extends inwardly, then upwardly through bottom wall 29, and top wall 27 of holder 21. After passing through top wall 27, the tube 51 extends inwardly and downwardly into funnel 33 via the open inlet end 35 of the funnel, terminating in an open outlet end 53 lying just within funnel 33.

The support arm 23 on which is mounted holder 21 has a cantilevered arm 61 extending laterally from a base 63 which normally lies against wall 7 of cabinet 3. The free end 65 of arm 61 has a circular pad 67 thereon, on top of which holder 21 is centrally positioned. A hole 69 extends through the center of the pad 67 and the funnel extension 39 extends through this hole 69 to help center and retain holder 21 on arm 23. A bearing 71, set in pad 67, rotatably supports holder 21 on pad 67 so it is free to rotate on pad 67 about a vertical axis.

Suitable drive means 73, as shown in FIG. 2, are provided for rotating the holder 21 when supported on pad 67. The drive means 73 can comprise a drive motor 75 mounted within cabinet 3 adjacent wall 7. The drive motor 75 has a drive shaft 77 which projects horizontally through wall 7 to lie beneath holder 21. A second, idle shaft 79 is rotatably mounted in wall 7 above, and parallel to, drive shaft 77. Pulleys 81 are mounted at the free ends 83, 85 of shafts 77, 79 respectively, and a friction drive belt 87 is mounted over pulleys 81. The drive means 73 are positioned so that drive belt 87, at the top of its run, engages bottom wall 29 of holder 21 adjacent side wall 31. Motor 75 drives belt 87 to rotate holder 21 about the vertical axis when mounted on pad 67.

The support arm 23 is preferably pivotably mounted to side 7 of cabinet 3. To this end, as shown in FIGS. 2 and 4 a pair of brackets 91, 93 are attached to the side 7 of cabinet 3. Pivot pins 95, 97, projecting from either side of the top 99 of base 63 of the support arm 23 are rotatably mounted in the brackets. The pivotable mounting allows the support arm 23, with holder 21 removed to be swung up and away from tissue treatment component 9, thereby allowing removal of component 9 from cabinet 3. Base 63 of arm 23 normally lies flat against wall 7 to retain arm 23 in its correct support position.

The side wall 31 of the holder 21 preferably has a rim 101 depending below bottom wall 29 as shown in FIGS. 2 and 4. A series of holes 103 are provided in the rim 101, each hole 103 located on a radial line 105 passing from the center of the holder 21 through the center of a chamber 41. The holes 103 are used in controlling the rotational movement of holder 21. Sensing means 107, which can comprise a light source 109 on one side of rim 101, and a light sensitive receiver 111 on the other side of rim 101, are connected to a central control 115 to control the movement of the holder 21 using holes 103 as will be described.

Storage cylinder emptying means 121, as shown in FIGS. 1 and 2 are provided on cabinet 3, operatively associated with holder 21. The emptying means 121 has a movable clamping head 123 mounted from a casing 125 which, in turn, is mounted on shelf 5 of cabinet 3 by a post 127. The casing 125 is rotatably mounted on post 127 to swing off or over holder 21. A portion of the casing 125 including head 123, is located over holder 21. The clamping head 123 is more particularly pivotably mounted to the arms of a U-shaped bracket 129 by pins 131. The bracket 129 in turn is mounted to a rod 133 projecting down from a solenoid 135 carried within casing 125. Actuation of solenoid 135 lowers head 123 down onto holder 21, and more particularly, down onto the cover 45 of one of the chambers 41. The head 123 has a central, through bore 137 through which a hose 139 is passed. The hose 139 serves to conduct air, under pressure, from a source to be described, into chamber 41 through hole 47 in cover 45, as head 123 is clamped down on cover 45. The period during when pressurized air is passed into the selected chamber, via line 139, is controlled by central control 115, as will be described.

Figure 3:
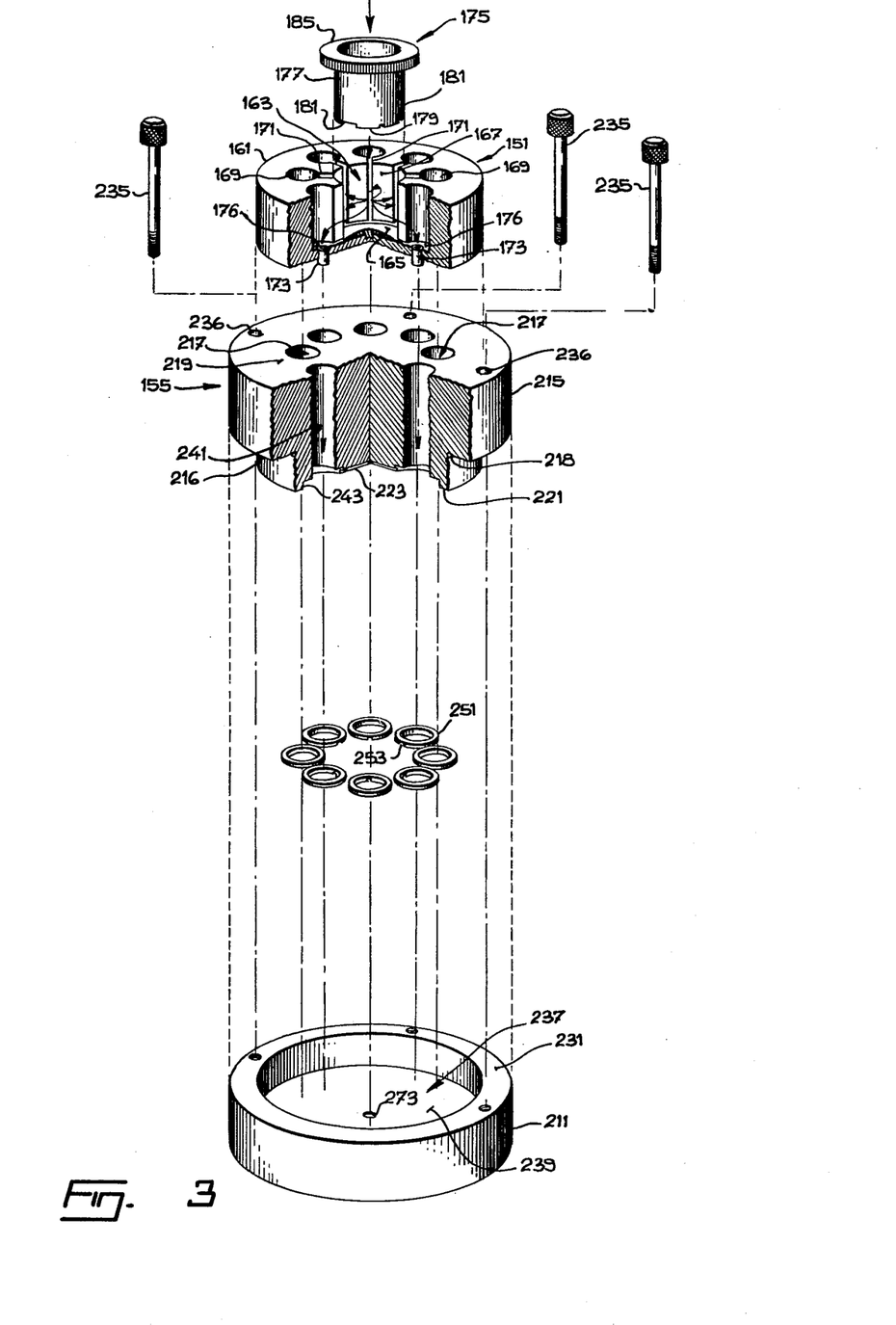
FIG. 3 is an exploded detail view, in partial section, of the treatment component of the apparatus.

The tissue treatment component 9 comprises liquid distributing means 151, tissue mounting means 153, and treating means 155 as shown in FIGS. 2 and 3. The liquid distributing means 151 comprise a cylindrical distributor 161 having a main, central liquid distributing well 163 which receives liquid from funnel 33 via tubular extension 39. The bottom of well 163 has a central domed portion 165 sloping down toward its cylindrical sidewall 167. A ring of secondary, liquid distributing wells 169 surrounds main well 163 in cylindrical distributor 161. Radial channels 171 connect main well 163 to the secondary wells 169. An outlet 173 is located in the bottom wall 175 of each secondary well 169.

A flow regulator 176 is preferably mounted within the main well 163. The flow regulator 175 can comprise a cylindrical tube 177 which fits snugly within well 163. The bottom annular wall 179 of tube 177 rests on bottom wall 165 of well 163 adjacent side wall 167. Outlets 181 are provided in the bottom of tube 177. The outlets 181 can comprise notches extending up from bottom wall 179 in tube 177. The notches are of varying width and spacing with the width and spacing selected so that the regulator 175 can be rotated within well 163 to provide liquid access to a various number of the secondary distributing wells 169 from central well 163. Regulator 175 is provided with a serrated rim 185 at its top end by which it can be rotated within main well 163 to select those secondary wells 169 which will be provided with liquid from main well 163 via notches 181 and radial channels 171.

The tissue specimens to be treated are mounted in tissue mounting means 153. These tissue mounting means 153, as shown in FIG. 2, comprise a plurality of cylindrical tissue specimen holders 195 stacked one above the other. Each holder 195 comprises a main tubular body 196 the lower end of which is provided with a relatively short coaxial annular extension 197 of smaller diameter. A cylindrical recess 198 of the same diameter and length as extension 197 is provided in the middle of the upper end of each body 196 to receive the extension 197 of the adjacent holder stacked just above, if any. A mesh or screen 201 is located in the recess 198 of each holder 195 to close the open end of the adjacent holder stacked just above. While three holders 195 are shown stacked one above the other in FIG. 2, more or less holders 195 can be employed.

The tissue mounting means 153 are mounted within the treating means 155. The treating means 155, as shown in FIG. 3 comprises a mounting base 211 and a treating cylinder 215. The treating cylinder 215 has a plurality of treating chambers 217 arranged in a ring.

Each chamber 217 comprises a cylindrical hole 241 having an enlarged bottom end portion 243 extending through cylinder 215 from its top face 219 to its bottom face 221. Shallow radial grooves 223 are provided in the bottom face 221 of cylinder 215. Each groove 223 extends from each enlarged end portion 243 to the middle of cylinder 215. The treating cylinder 215 sits on the top surface 231 of mounting base 211 and is properly positioned by means of a shoulder 216 extending inwardly near the lower end of the side wall of cylinder 215. Bolts 235 pass down through holes 236 in cylinder 215 to thread into base 211 and thus connect cylinder 215 to the base. An O-ring 218 is interposed between the base 211 and shoulder 216 to provide sealing, the surface of the shoulder 216 being flush with the top surface 231 of base 211.

The base 211 has a shallow central well 237. Rings 251 are provided for closing completely or partially the bottom of each chamber 217 in cylinder 215. These rings 251 are inserted into the enlarged bottom end portions 243 of the chambers 217 and rest on bottom wall 239 of the well 237 thus providing sealing. Each ring 251 is provided with a shallow radial groove 253 in one of its faces. When the face of ring 251 provided with groove 253 is inserted first in the enlarged end portion 243, the corresponding chamber 217 is completely closed. When the face of ring 251 provided with groove 253 rests on bottom wall 239 of base 211, the corresponding chamber 217 is connected through groove 253 to an outlet 273 in the middle of the bottom wall 239 of the well 237.

The rings 251 advantageously hold in position the tissue mounting means 153 within the chambers 217 as shown in FIG. 2. A filter made from glass fiber material, and a mesh or a screen not shown can be inserted into each enlarged bottom end portion 243 prior to inserting ring 251 therein, to filter the liquid, if desired.

Figure 6:
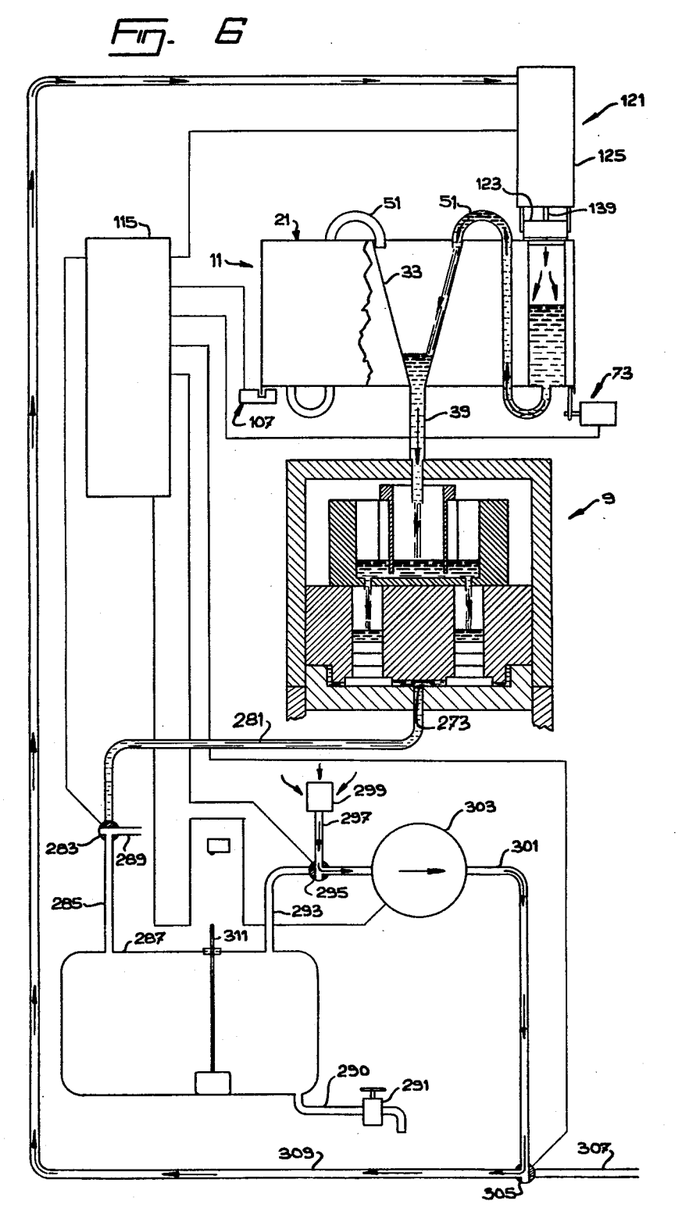
FIG. 6 is a schematic view of the apparatus during one phase of operation.
Figure 7:
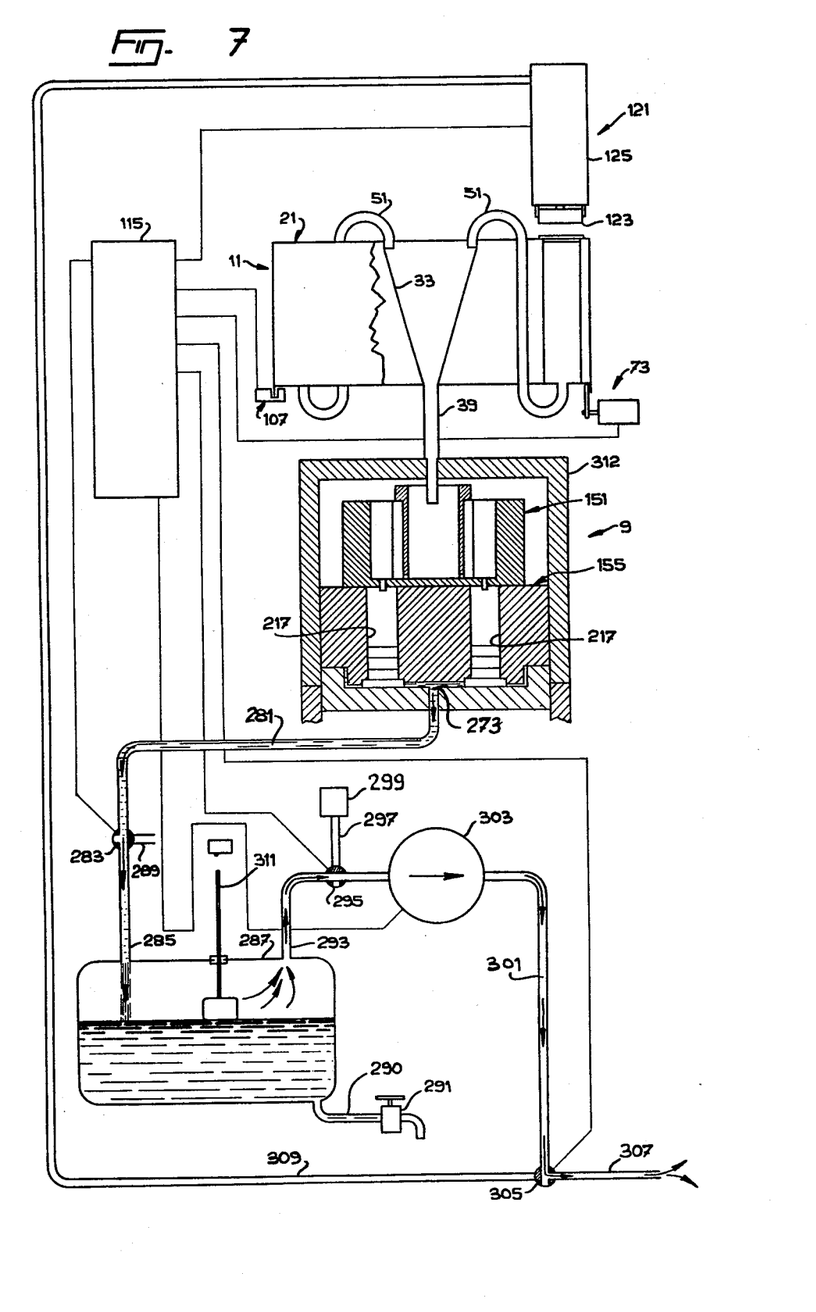
FIG. 7 is a schematic view of the apparatus during another phase of operation.

Now referring to FIGS. 6 and 7, outlet 273 from well 237 is selectively connected, via a line 281 and a valve 283, to a line 285 leading to a holding tank 287 or a to vent line 289 for tank 287.

The bottom of the tank 287 has a drain line 290 for use in manually draining it. A shut-off valve 291 is provided in line 290. A line 293 leads from the top of tank 287, to a valve 295. Valve 295 selectively connects a line 297 leading from an air intake 299, to line 293, and thus to tank 287, or to a line 301 passing to a pump 303 and to another valve 305. Valve 305 selectively connects line 301 to a vent line 307 or a feed line 309 passing to casing 125 in the chamber emptying means 121 where it connects to line 139. The tank 287 can have a float operative safety switch 311 for switching off the apparatus to prevent liquid from passing out line 293 if the tank 287 gets too full.

It is often necessary to have the tissue treating liquid within same specific temperature range when treating the tissue. To this end, the tissue treatment component 9 is temperature controlled. An insulating shell 312 is mounted about component 9 as shown in FIG. 2. The tubular extension 39 of funnel 33 passes through a bushing 314 mounted in shell 312. The bushing 314 can be made of Teflon, or similar suitable material. The temperature within the treating means 155 is controlled by mounting thermo-electric heating and/or cooling elements 315, known as peltier elements, under the bottom wall of base 211. An extension 319 to base 211 provides a chamber 321 to hold a cooling liquid for cooling elements 315. The chamber 321 has an inlet 325 and an outlet 327 for circulating the cooling fluid through chamber 321 to control the temperature in well 237 of base 211. A temperature sensor, not shown, is mounted in the treating means 155 to sense the temperature thereof, and to control the operation of the temperature regulating means.

The cabinet 3 houses the control means 115 for operating the apparatus. The control means 115 operates valves 283, 295 and 305; motor 75; sensor 107; pump 303; and solenoid 135.

In operation, the tissue specimens to be treated, are mounted in the holders 195 of the tissue mounting means 153. The tissue mounting means 153 are then mounted within chambers 217 on top of rings 251. The different liquids, used to treat the tissue specimen, are poured into storage cylinders 43 in holder 21. Each storage cylinder 43 can carry a different liquid. The nearly full cylinders 43 are then tightly closed by covers 45. The control 115 can be programmed to treat the tissue specimens with the different liquids in a specific sequence. To treat the tissue specimens with the first liquid selected, the drive motor 75 is operated to rotate holder 21 to bring the cylinder 43 carrying the first selected liquid under head 123. The sensing means 107 controls the operation of motor 75 via control 115 until the desired cylinder 43 is under head 123. Control 115 operates valve 283 to close line 281 and to open line 289 to vent tank 287; valve 295 is operated to close line 293 and open line 301 and valve 305 is operated to connect line 301 to line 309 and thus line 139. Solenoid 135 is operated to lower head 123 onto the cover 45 and to thus connect hose 139 to opening 47 in cover 45. Pump 303 is then operated to draw air in from inlet 299 through line 297 and to pump this air under pressure through lines 301, 309 and 139 into the top of the selected cylinder 43. This causes the liquid in the cylinder to be passed through tube 51 into funnel 33 and down into the flow regulator 175 positioned with distributor 161. The flow regulator 175 has been rotated before so as to direct the liquid through notches 181 into selected slots 171 and then into chambers 169 overlying some selected chambers 217 carrying tissue mounting means 153. The liquid pushed out of the selected cylinder flows down into the selected chambers 217 carrying the tissue specimens and fills up the well 237 and through grooves 223 the lower part of all of the chambers 217 except those which have been completely closed by means of rings 251.

Valve 283 closing line 281 leading out from well 237, a substantial portion of liquid is retained in the chambers 217. Simultaneously, vibrating means 8 connected with the tissue treatment component 9, are switched on to increase the Brownian movement of the liquid and agitate it through holders 195 to wash and treat the tissue specimens located therein. The liquid stays in chambers 217 for the length of time necessary to treat the tissues. After this period of time, valve 283 is moved to connect line 281 to tank 287, and valve 295 is moved to close line 297 and open line 293 to line 301. Valve 305 is moved to connect line 301 to line 307. Continued operation of pump 303 now empties liquid from chambers 217 moving the liquid out of well 237 through line 281 into tank 287. The tank vents through line 301. Solenoid 135 releases head 123 and motor 75 is operated by control 115 to rotate the holder 21 to bring the cylinder 43 containing the next desired treating liquid under head 123. The procedure is then repeated to treat the tissue specimens in the same manner as before with this second liquid.

The tissue specimens may be treated in this manner with a variety of liquids to obtain desired results. The length of times of treatment may vary for each liquid. During the treatments, the heating and/or cooling frigistors 315 may be operated while a cooling liquid is circulated through chamber 321, to regulate the temperature with the insulating casing 312 and within well 237.

When treatment of the tissue specimens has been completed, holder 21 can be raised, through arm 23 pivoting about pivot 595 and 97. Insulating casing 312 is removed, distributor 151 is lifted off treating means 155 and the treated tissue specimens are removed from tubes 196.

The entire treatment cycle employing many different liquids, can, with a timer and a program in control 115, be done accurately and automatically.

I claim:

1. Apparatus for use in treating cellular material with a plurality of liquids, comprising:

(A) a tissue treatment component, comprising:
      (a) a treating element having a plurality of treating chambers arranged in a circle about a vertical axis, each treating chamber having a liquid inlet at its top and a liquid outlet at its bottom;
      (b) a mounting base for receiving and supporting said treating element, and having a liquid outlet to which are connected said liquid outlets of all the treating chambers of said treating element;
      (c) tissue mounting means receivable within said treating chambers, for supporting cellular material to be treated; and
      (d) liquid distributing means arranged to distribute liquid to said liquid inlets of said treating chambers, including a distributor element having a main central liquid distributing well and a plurality of secondary liquid distributing wells arranged in a circle about said main well, each of said secondary wells being connected with said main well to receive liquid therefrom, and with a corresponding one of said treating chambers to discharge liquid thereto; and (B) a liquid supply component arranged to supply liquid to said main well of said distributor element, comprising:
      (a) a rotatably mounted liquid holder having a main liquid outlet and a plurality of separate liquid storage chambers arranged in a circle about a vertical axis for carrying a plurality of treating liquids, each of said storage chambers having an inlet in its top and a liquid outlet, and said main liquid outlet being arranged to discharge into said main well of said distributor element; and conduit means connecting said liquid outlets of all of said storage chambers with said main liquid outlet;
      (b) storage chamber emptying means operatively associated with said liquid holder, including: a vertically movable head mounted above said circle of liquid storage chambers, said storage chambers being alignable with said head as said liquid holder is rotated; means arranged and operable to move said head downwardly onto the top of a selected one of said storage chambers to tightly close the same and to return said head to an elevated position when desired, said movable head carrying conduit means that is connected with said inlet of the associated storage chamber when said head is moved downwardly to close the top of the chamber; and means operable for introducing compressed air through said conduit means of said vertically movable head into said selected storage chamber while said head is pressed against the top of said chamber, for causing the liquid carried within the selected storage chamber to move into said treating chambers via said main liquid outlet and said liquid distributing means; and
      (c) drive means for rotating said liquid holder for selectively positioning said storage chambers under said vertically movable head.

2. An apparatus as claimed in claim 1, further including: sensing means to control said drive means, to position each selected storage chamber under said movable head.

3. An apparatus as claimed in claim 1, further including: a flow regulator mounted within said main well of said distributor element, and adjustable to selectively adjust the quantity of treating liquid to be distributed to each secondary well.

4. An apparatus as claimed in claim 3, wherein said main well is cylindrical, and wherein said flow regulator comprises a cylindrical tube fitting snuggly within said cylindrical main well, and provided with a plurality of outlets of varying width and spacing, said outlets of said tube being selectively connectable with said secondary wells by adjusting the position of said tube.

5. An apparatus as claimed in claim 1, wherein said tissue mounting means includes at least one tissue specimen holder, said specimen holder being in the shape of a cylinder having, at its lower end, a short coaxial extension of small diameter, and at its upper end, a cylindrical recess of substantially the same diameter and length as said extension, said recess being closed by material permeable to air and liquid.

6. An apparatus as claimed in claim 1, further including: means for controlling the temperature in said treating chambers.

7. An apparatus as claimed in claim 1, further including: means at the bottom liquid outlet of each of said treating chambers, adjustable to selectively partially or completely close off the outlet of said treating chamber from said liquid outlet of said mounting base.

* * * * *